United States Patent [19]

Kurono et al.

[11] Patent Number: 5,459,049
[45] Date of Patent: Oct. 17, 1995

[54] MOTILIN-LIKE POLYPEPTIDE AND USE THEREOF

[75] Inventors: Masayasu Kurono; Takahiko Matani; Haruo Takahashi; Kenichi Tanaka; Katsuya Fujimura; Yuji Hayashi; Yohei Kobayashi; Kiichi Sawai, all of Nagoya, Japan

[73] Assignee: Sanwa Kagaku Kenkyushko Co., Ltd., Aichi, Japan

[21] Appl. No.: 3,688

[22] Filed: Jan. 13, 1993

Related U.S. Application Data

[60] Continuation of Ser. No. 665,836, Mar. 7, 1991, abandoned, which is a division of Ser. No. 459,236, Dec. 29, 1989, abandoned.

[30] Foreign Application Priority Data

| Jan. 6, 1989 | [JP] | Japan | 64-286 |
| Aug. 24, 1989 | [JP] | Japan | 1-216034 |
| Nov. 8, 1989 | [JP] | Japan | 1-288730 |

[51] Int. Cl.⁶ .................. C07K 14/63; C12N 15/16; C12N 15/63; C12N 15/67
[52] U.S. Cl. .................. 435/69.4; 435/69.8; 435/320.1; 530/324; 536/23.51
[58] Field of Search .................. 435/69.1, 69.7, 435/69.8, 252.3, 172.3, 320.1, 820, 69.4; 530/300, 324; 536/23.5, 24.1, 24.2, 23.51; 935/39, 42, 48, 51

[56] References Cited

FOREIGN PATENT DOCUMENTS

| 0259891 | 3/1988 | European Pat. Off. |
| 0289995 | 9/1988 | European Pat. Off. |
| 0378078 | 7/1990 | European Pat. Off. |
| 63-71195A | 3/1963 | Japan |

OTHER PUBLICATIONS

Brown et al., *Gastroenterology*, 62, pp. 401–404 (1972).
Schubert et al., *Can. J. Biochem.*, 52, pp. 7–10 (1974).
Christofides et al., *Gastroenterology*, 80, pp. 456–460 (1981).
Strunz et al., *Scand. J. Gastroenterology*, 11, pp. 199–203 (1976).
Seino et al., *FEBS Letters*, 223, pp. 74–76 (1987).
Sung, W. L. et al. *PNAS* 83:561–565 (1986).

*Primary Examiner*—Robert A. Wax
*Assistant Examiner*—Dian C. Jacobson
*Attorney, Agent, or Firm*—Nikaido, Marmelstein, Murray & Oram

[57] ABSTRACT

A process for the preparation of a polypeptide of the formula

Phe—Val—A'—Ile—Phe—Thr—Tyr—B'—Glu—Leu—C—

—Arg—X'—Gln—Glu—Lys—Glu—Arg—D—Lys—Gly—E—Y' wherein A' is Pro, Gly, Asp or Ser; B' is Gly, Asn or Ser; C is Gln, Glu or Asp; D is Asn, Glu or Asp; X' is a residue of amino acid other than Met; E is Gln, Lys or Arg, and Y' is a residue of homoserine or homoserine-lactone, as well as a recombinant DNA and expression plasmid for preparing the polypeptide.

4 Claims, 5 Drawing Sheets

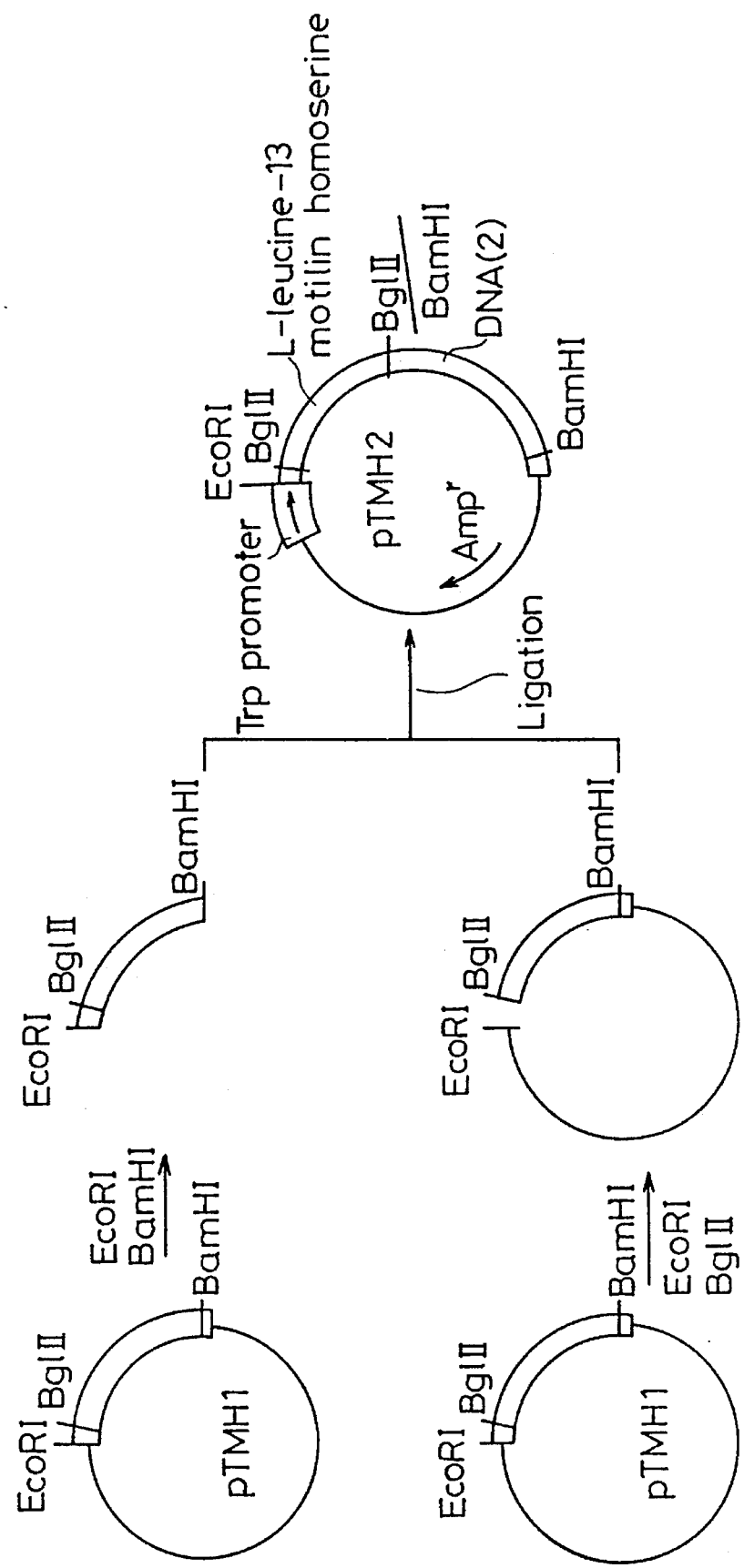

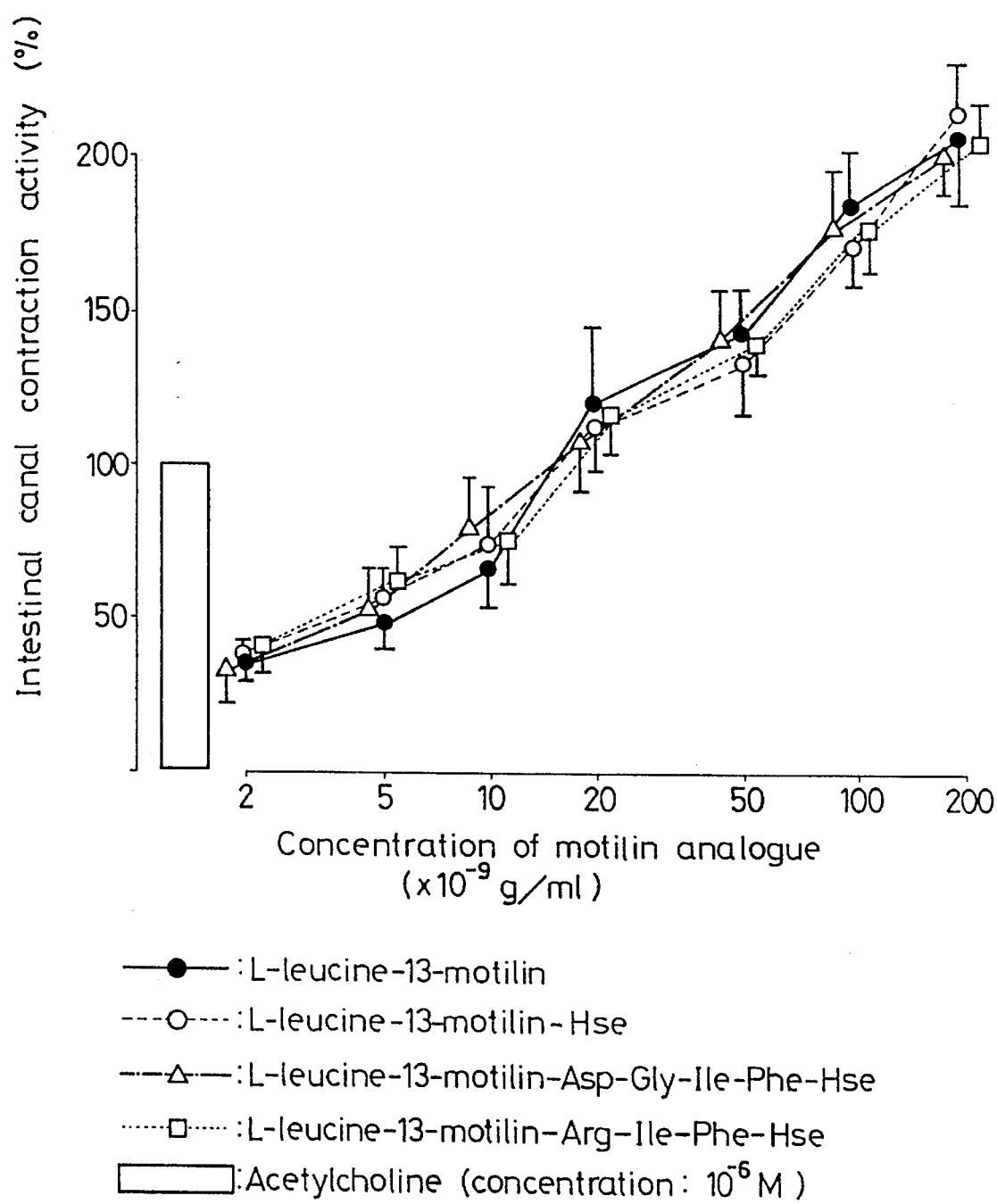

MOTILIN-LIKE POLYPEPTIDE AND USE THEREOF

This application is a continuation of application Ser. No. 665,836 filed Mar. 7, 1991, now abandoned which is a division of application Ser. No. 459,236 filed Dec. 29, 1989, now abandoned.

BACKGROUND OF THE INVENT ION

1. Field of the Invention

The present invention relates to a motilin-like polypeptide, namely a polypeptide having a pharmacological activity similar to motilin, a salt thereof, a process for the preparation of the polypeptide, a recombinant DNA thereof, and a plasmid for expressing the polypeptide as well as a use of the polypeptide for curing gastro-enteropathies.

2. Related Arts

Motilin is one of the peptide hormones, first isolated from the mucous membrane of porcine upper small intestine, and its amino acid sequence determined by Brown J. C. et al ["Gastroenterology", Vol. 62, pages 401–404 (1972) and "Can. J. Biochem.", Vol. 52, pages 7–10 (1974)]. The porcine motilin consists of 22 amino acids and has molecular weight of about 2700.

While, some of the present inventors have succeeded in isolation of cloned cDNA encoding human motilin precursor, the nucleotide sequence therein including a part designating the amino acid sequence same with that for the Porcine motilin, so that it has been made apparent that the human motilin has the amino acid sequence same with that for the porcine motilin [Jap. Pat. No. Sho 63-276489(A) which corresponds to United States Pat. application Ser. No. 07/190,849 and European Pat. Appln. No. 88107108.81].

Regarding the physiological activities of motilin, a hypermotility action of digestive tract and contracting action of gastroduodinal and colonic smooth muscle therein have been well known. As the hypermotility action, it has been reported that the rate of gastric emptying is shortened ["Gastroenterology", Vol. 80, pages 456–460 (1981)] and as the contracting action of smooth muscle in the digestive tract, it has been known that motilin shows a strong contracting action to a rabbit and human gastrointestinal tract, independent from a neuro system. Moreover, no report has been issued on any specific side-effect. Therefore, it has been considered that the motilin is useful for curing gastro-enteropathys at the period of post-operation and for diagnosis thereof. In connection with this, please note that prostagrandin has widely been employed for curing gastro-enteropathies, although the drug shows a relatively strong sideeffect.

It has also been reported that chemically synthesized motilin analogue -methionine residue at 13-position of motilin being substituted with leucine or norleucine residue- shows biological activity similar to pure native porcine motilin ["Scand. J. Gastroenterology", Vol. 11, pages 119–203 (1976) and others]. Therefore, it has been considered that methionine residue at 13-position has almost no influence on useful activity of the motilin.

The motilin according to widely accepted technical art has been obtained through an extraction from porcine organ tissue and thus it was quite difficult to obtain the same in large amount. Since the motilin is a polypeptide consisting of 22 amine acids, a large scale production is difficult and a cost thereof becomes higher, even if a chemical synthesis shall be applied therefor. Namely, the motilin has not actually been employed for clinical use, due to its poor productivity, despite the expected effectiveness of the drug for curing gastroenteropathies.

Therefore, various studies have been made for preparing polypeptides having motilin-like biological activity, with a reasonable cost, by utilizing the so-called "Biotechnology" [Jap. Pat. Nos. She 63-71195(A) and 63-208006(A)].

Further, such studies have also been made to develop motilin analogues showing biological activities higher than those of the motilin per se [Jap. Pat. No. Sho 61-26559(B)].

All of said processes utilizing Biotechnology comprise a step for cleaving a polypeptide chain with use of cyanogen bromide, and a step for removing an excess peptide chain containing homoserine at C-terminal, with use of an enzyme. However, the enzymatic treatment reduces the yield of a desired motilin analogue and increased the cost thereof, which makes a large scale production of the motilin analogue difficult.

SUMMARY OF THE INVENTION

A principal object of the invention is to provide a novel motilin-like polypeptide having a biological activity equal to or higher than that of native motilin, and a salt of the polypeptide.

First additional object of the invention is to provide a pharmaceutical agent, namely the agent for curing gastro-enteropathys which contains as an effective ingredient the motilin-like polypeptide or salt thereof.

Second additional object of the invention is to provide a process for the preparation of the motilin-like polypeptide or a salt thereof, which is easier than any process developed prior to this invention, so that the polypeptide and a salt thereof can be supplied to the market with a reasonable price and in large amount.

Third additional object of the invention is to provide a novel recombinant DNA to be employed for carrying out said process.

Fourth additional object of the invention is to provide a plasmid, in which the recombinant DNA is inserted to express the motilin-like polypeptide.

It has been estimated that a pharmacologically active part of the motilin lies in the region of from N-terminal to 15-position in its amino acid sequence ["Peptide Chemistry 1977", pages 171–176 (1978)]. Characteristic of the region lies in that 7 residues of hydrophobic amino acids of phenylalanine (Phe, appearing in double), valine (Val), proline (Pro), isoleucine (Iie), glycine (Gly) and leucine (Leu) appear in the positions of 1–10. Under the assumption that a hydrophobicity in the region has a certain relation to a generation of pharmacological activity in the motilin, namely to a binding with a motilin receptor on cell membrane of colonic smooth muscle of rabbit ["Regulatory Peptides", Vol. 15, pages 146–153 (1986)], the present inventors have chemically synthesized various motilin analogues and investigated the same by taking mainly amino acids in the region of 1–10 positions into consideration and finally found that the pharmacological activity thereof can be increased by substituting the amino acid residues in the region for the native motilin with suitable amino acid residues.

Further, the present inventors have also unexpectedly found that the polypeptide per se obtained through the cleaving step using cyanogen bromide and not yet treated with an enzyme has a pharmacological activity equal to or higher than that of the native motilin. This means that the enzymatic removal treatment of residues of amino acids including homoserine (including homoserine-lactone and referred to hereinafter as "Hse") is not required.

According to one aspect of the invention, therefore, the principal object can be attained by a polypeptide of the formula

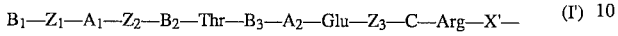

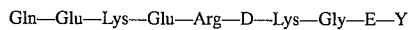

wherein $Z_1$, $Z_2$ and $Z_3$ are a residue of amino acid having a hydrophobic side-chain, $A_1$ and $A_2$ are a residue of amino acid which can take a turn structure in the polypeptide chain, $B_1$, $B_2$ and $B_3$ are a residue of amino acid having a side-chain with an aromatic ring, Gln, Glu or Asp, D is Asn, Glu or Asp, X' is a residue of amino acid other than Met, E is Gln, Lys or Arg, and is OH, homoserine, homoserine-lactone or a peptide chain having amino acid residues not exceeding 10 and containing homoserine or homoserine-lactone at C-terminal, and a salt thereof.

As the amino acid having the hydrophobic side-chain, valine (Val), isoleucine (Ile), leucine (Leu) or the like can be listed. As the amino acid which can take the turn structure in the polypeptide chain, proline (Pro), glycine (Gly), asparagine (Asn), serine (Ser) or the like can be listed.

The reason why the symbol X' for 13-position amino acid residue is stated as the residue of amino acid other than methionine (Met) lies in that if X' is a Met residue, the desi red polypeptide having the motilin-like activity can not be obtained, since a cleavage will also occur at Met in 3-position, when a fused protein is treated with the cyanogen bromide. However, the amino acid residue at 13-position may be made as Met, in which case the Met residue shall be protected with a protecting group with use of a suitable chemical procedure to prevent any cleavage at that position due to the cyanogen bromide treatment, the resulting polypeptide with the protected Met residue at 13-position is treated with cyanogen bromide to form homoserine or homoserine-lactone residue at C-terminal, and then the protection radical for the Met is removed.

Therefore, the polypeptide according to the invention is characterized substantially by that shown by the formula of

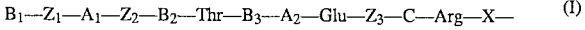

wherein $Z_1$, $Z_2$, $Z_3$, $A_1$, $A_2$, $B_1$, $B_2$, C, D, E and Y have the the meanings as referred and X is an optional amino acid residue, and a salt thereof which have motilin-like biological activities.

The first additional object can be attained by a pharmaceutical composition for curing a gastoroenteropathy, which comprises, an effective amount of at least one of the polypeptides shown by said formula (I) and salts thereof, in association with a pharmaceutically acceptable carrier or excipient.

Among the polypeptides shown by said formula (I), those shown by the formula of

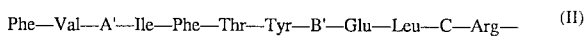

wherein C, X', D and E have the meanings as referred to, A' is Pro, Gly, Asn or Ser, B' is Gly, Asn or Ser, and Y' is homoserine, homoserine-lactone or a peptide chain having amino acid residues not exceeding 10 and containing homoserine or homoserine-lactone at C-terminal, can be prepared through steps of synthesizing a single-stranded DNA which encodes a peptide having at least 6 residues of uncharged polar amine acids and methionine at its terminal, a single-stranded DNA encoding the amine acid sequence shown by said formula (II) and methionine at C-terminal, and a single-stranded complementary DNA; preparing a double-stranded DNA with use of said single-stranded DNA having a specific restriction enzyme recognition site, respectively; ligating a specific restriction site of an expression vector with use of the restriction enzymes same with said specific ones; reconstructing a plasmid having multiple joined genes; introducing the reconstructed plasmid into a microorganism to cause a transformation of the microorganism; cultivating the resulting transformant to produce therein a polypeptide having the amino acid sequence of the formula (II) with the exception of having methionine at C-terminal, as a part of fused protein; breaking the microorganism and treating the same with cyanogen bromide to separate the polypeptide of the formula (II) from the fused protein; and fractionating the resulting mixture to isolate the desired polypeptide of the formula (II), so that the second additional object can be attained.

The ground of that the symbol Y' at C-terminal in the formula (II) is stated as the residue of homoserine, homoserine-lactone or a peptide chain having the amino acid residues not exceeding 10 and containing homoserine or homoserine-lactone at C-terminal lies in obtaining the desired polypeptide having the motilin-like activity, by only the step of treating the fused protein with use of the cyanogen bromide. As the uncharged polar amino acid, asparagine (Asn), glutamine (Gln), threonine (Thr) and serine (Ser) are suitable for increasing an expression rate of the desired polypeptide.

For producing the polypeptide in large amounts in a microorgansim, a fused protein is prepared containing the polypeptide having the amino acid sequence of formula (II) with the exception of having methionine (Met) at the C-terminal (Note : Met will be removed by the treatment with cyanogen bromide, so that Hse wit I appear at C-terminal). It is important to ligate a plural number of the polypeptide having Met at C-terminal in tandem arrangement, so as to express the motilin-like polypeptide as a polymerized protein. This can be done by using techniques given in the specification for Jap. Pat. Appln. No. Sho 63- 208006 (corresponding to United States Pat. Appln. Ser. No. 07/390149 and European Pat. Apptn. No. 89115199.5). It is sufficient that each of the motilin-like polypeptides to be tandemly arranged has methionine at C-terminal, since the treatment with use of the cyanogen bromide will cause a cleavage of the polymerized protein at each part of methtonine, whereby the polymer protein is separated into its constitutional monomer proteins.

As apparent from the descriptions given above, the third additional object can be attained by the recombinant DNA which encodes the leader sequence polypeptide having at least 6 residues of the none-charged polar amino acids, and subsequently encoding the motilin-like polypeptide having the amino acid sequence of the formula (II), but with the exception of having methionine (Met) at C-terminal. In this case, it is preferable that a plurality of the motilin-like polypeptide are connected in tandem arrangement, wherein each polypeptide has Met at its C-terminal.

The last of fourth additional object can be attained by the expression plasmid, wherein such a recombinant DNA is inserted.

BRIEF DESCRIPTION OF THE DRAWING

FIG. 2 is an illustration showing steps for inserting two tandemly arranged motilin-like genes into a plasmid;

FIG. 3 is a graph showing results of that an intestinal contract ion activity was measured by Magnus method and compared, on motilin-like polypeptides according to the invention, as test samples and a conventional pure [Leu$^{13}$]-motilin, as control sample, when an contraction activity of $10^{-6}$M acetylcholine is assumed as 100%;

DETAILED DESCRIPTION OF THE PREFERRED EMBODIMENTS

Figure 1:
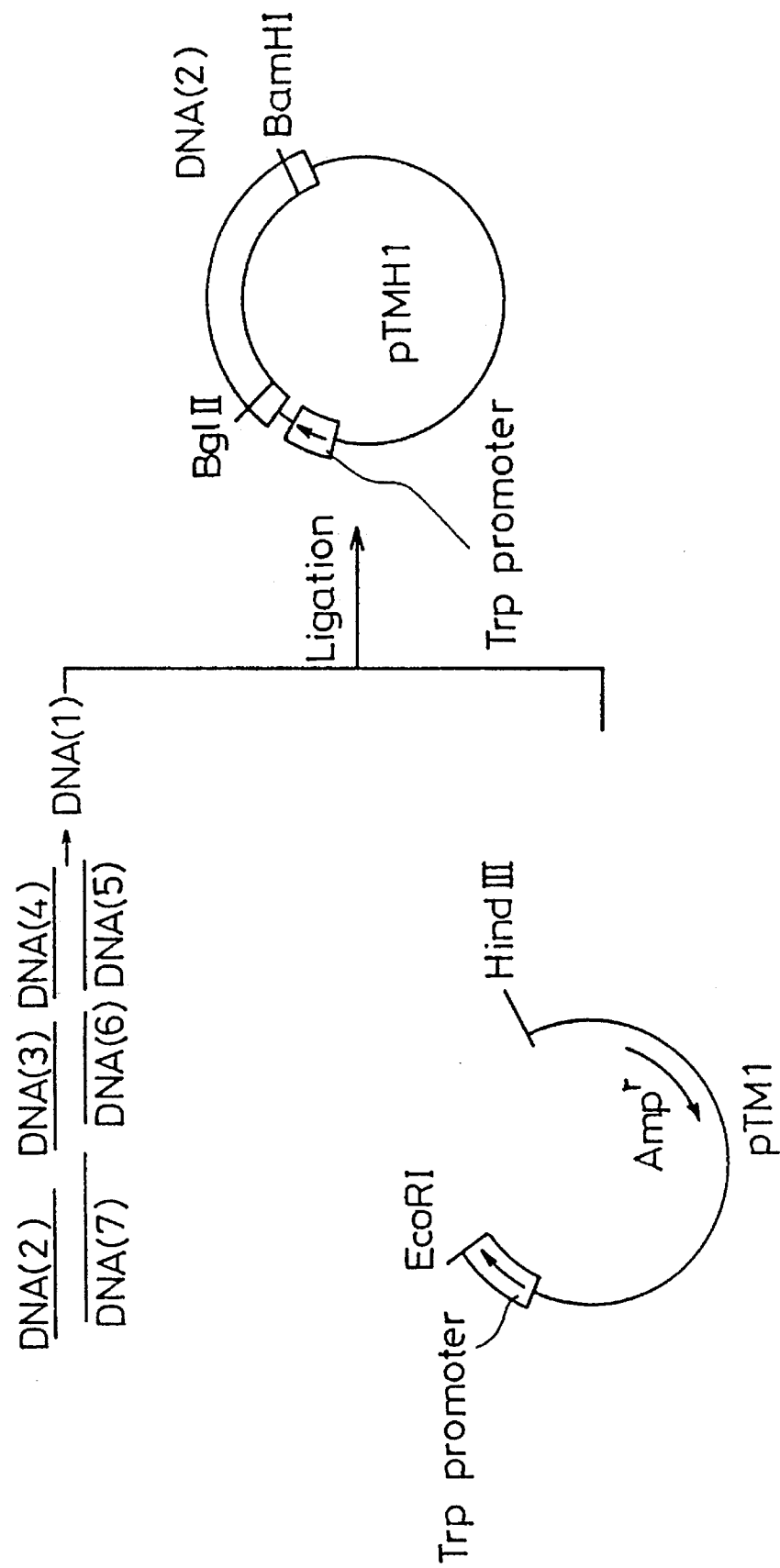
FIG. 1 is an illustration showing steps for inserting one motilin-like gene into a plasmid.

The invention will now be further explained with reference to Examples, Test Examples on pharmacological activity, and Medicine Preparation Examples.

In the following, the explanation will be given on motilin analogues, in which methionine residue at 13-position of native motilin is modified into leucine residue, but please note that other and various motilin analogues having an amino acid residue other than methionine residue at 13-position, can be prepared in a similar manner by using a fermentation method, and that motilin analogues having methionine residue at 13-position may also be prepared by protecting the methionine residue with use of a chemical synthetic method to prevent a cleavage at that position, then treating with cyanogen bromide to form homoserine or homoserine-lactone at C-terminal and thereafter removing the protecting group for the methionine residue.

EXAMPLE 1

In the first place, polypeptides, each having following amine acid sequence were synthesized with use of a peptide synthesizer (Type 430A marketed by Applied Biosystems Co.).

```
 1    2    3    4    5    6    7    8    9   10
Phe — Val — Pro — Ile — Phe — Thr — Tyr — Gly — Glu — Leu —
```

-continued

```
11    12    13    14    15    16    17    18    19
Gln — Arg — Leu — Gln — Glu — Lys — Glu — Arg — Asn —

20    21    22    23
              Lys — Gly — Gln — R₁,
``` wherein R$_1$ is a) Met-Gly-Ser, b) Asp-Gly-Ile-Phe-Met-Gly-Ser, or c) Arg-Ile-Phe-Met-Gly-Ser.

A purification of each synthesized polypeptide was carried out by subjecting to HPLC under following conditions, with use of a μ Bondasphere C-18 column (19 mm×15 cm) marketed by Waters Co.

Eluate Linear gradient of 30% to 60% acetonitrile in 0.1% trifluoroacetic acid (30 minutes)

Flow rate : 7.0 ml/min.

Each of the purified samples (10 mg) was taken and dissolved in 70% formic acid solution (30 ml). After added 50 mg of cyanogen bromide, the solution was reacted for 16–24 hours under 37° C. Then, distilled water (200 ml) was added and lyophilized to remove the formic acid and cyanogen bromide. The resulting material was subjected again to HPLC under conditions same with the former, with use of a μ Bondasphere C-18 column marketed by Waters Co.

Fractions in a main peak part on the HPLC were recovered and lyophilized. A part of the dried powder was taken and a nucleotide sequence thereof was checked with use of a peptide sequencer marketed by Applied Biosystems Co. to confirm that each of the samples was correctly cleaved at the position of methionine (Met) and a polypeptide, wherein said R$_1$ at C-terminal is modified, as follows.

A) Hse,

B) Asp-Gly- Ile-Phe-Hse, or

C) Arg-Ile-Phe-Hse.

This Example explains the process for the preparation of motilin-like polypeptides, wherein the methionine (Met) in 13-position of motilin is changed to leucine (Leu), but other motilin-like polypeptide having another amino acid residue other than methionine residue in 13-position can be produced by a conventional fermentation method. Further, please note that still other motilin-like polypeptides, wherein a part of the amino acid residues is changed, can also be obtained by synthesizing in a manner similar to the aforesaid, with use of a peptide synthesizer, cleaving the same with use of cyanogen bromide, and purifying by HPLC.

EXAMPLE 2

(1) Synthesis of DNA encoding a polypeptide having motilin-like biological activity:

Motilin-like polypeptide, wherein Met in 13-position is replaced with Leu and Hse is added in 23-position, has the following amino acid sequence.

```
                  5                             10
Phe — Val — Pro — Ile — Phe — Thr — Tyr — Gly — Glu — Leu —

13              15
Gln — Arg — Leu — Gln — Glu — Lys — Glu — Arg — Asn —

20                        23
              Lys — Gly — Gln — Hse
```

It has been known on the polypeptide that Hse residue in 23-position is formed by modification of Met residue, when a fused protein produced by a microorganism is treated with cyanogen bromide.

Therefore, following double-stranded DNA fragment shown by following Formula (I) was synthesized, which includes a nucleotide sequence encoding an amino acid sequence having Met residue in 23-position of said amino acid sequence, has at N-terminal a nucleotide sequence encoding a leader polypeptide with a number of non-charged polar amino acid residues through Met (Met-Thr-Met-Ile-Thr-Asn-Ser-Gln-Gln-Gln-Gln-Gln-Gln-Ile-Phe-Met), and has at C-terminal a nucleotide sequence encoding a polypeptide which has an amino acid sequence of Gly-Ile-Leu.

position with distance of 10 residues from SD sequence in downstream of the Trp promoter. When the expression plasmid is inserted in *Escherichia coli* or the like, therefore, a protein shall be produced with use of indoleacrylic acid (IAA) or the like.

Further, the recombinant vector has been designed to have recognition sites for restriction enzymes of BglIl and BamH1.

(3) Construction of recombinant plasmid with two or more motilin-like genes:

This shall be explained with reference to FIG. 2.

In the first place, the recombinant plasmid (pTMH1) obtained in said Item 3 was treated with restriction enzymes

```
5'-AATTCATGACCATGATTACGAACTCACAACAACAACAACAGATCTTCATG          Formula (1)
3'-     GTACTGGTACTAATGCTTGAGTGTTGTTGTTGTTGTCTAGAAGTAC TTCGTTCCGATCTTCACCTACGGCGAACTGCAGCGTCTGCAAGAAAAAGAGCG
AAGCAAGGCTAGAAGTGGATGCCGCTTGACGTCGCAGACGTTCTTTTTCTCGC

CAACAAAGGCCAGATGGGGATCCTGTGATA
GTTGTTTCCGGTCTACCCCTAGGACACTATTCGA
```

The double-stranded DNA shown by Formula (1) was synthesized in a following manner.

In the first place, the following 6 single-stranded DNAs, each having following amino acid sequence, were synthesized with use of a DNA synthesizer (Gene Assembler, marketed by Pharmacia AB, Sweden). Among them, please note that each pair of DNAs of Formulae (2) and (7), (3) and (6) as well as (4) and (5) are complementary DNAs, excepting a part thereof.

of EcoRI and BamH1 to cut the same at an upper-stream position of the motilin-like gene part and at a potion in the vector part, so that a fragment was recovered. Another recombinant plasmid (pTMH1) was treated with restriction enzymes of EcoRI and BglIl to cut the same at the same position in the vector part and at a position for making a cleavage site common to that of the upper-stream cleavage position in a downstream region of the motilin-like gene part. To the cleavage sites, the previously recovered fragment was ligated with use of DNA ligase to obtain an

| | |
|---|---|
| AATTCATGACCATGATTACGAACTCACAACAACAACAACA | Formula (2) |
| GATCTTCATGTTCGTTCCGATCTTCACCTACGGCGAACTGCAG | Formula (3) |
| CGTCTGCAAGAAAAAGAGCGCAACAAAGGCCAGATGGGGATCCTGTGATA | Formula (4) |
| AGCTTATCACAGGATCCCCATCTGGCCTTTGTTGCGCTCTTTTCTTG | Formula (5) |
| CAGACGCTGCAGTTCGCCGTAGGTGAAGATCGGAACGAACATGAA | Formula (6) |
| GATCTGTTGTTGTTGTTGTGAGTTCGTAATCATGGTCATG | Formula (7) |

Each of the single-stranded DNAs shown by Formula (2)–(7) was treated with a polynucleotidekinase to phosphorylate at 5'-terminal, and each complementary DNA pair shown by Formula (2) and (2), (3) and (6) as well as (4) and (5) was annealed to prepare three double-stranded DNAs which were tandemly ligated with use of DNA ligase to obtain the DNA fragment shown by Formula (1).

(2) Insertion of DNA fragment into expression vector:

Operations for inserting the synthesized DNA fragment obtained in said Item 1 into an expression vector (plasmid) shall be explained with reference to FIG. 1.

A commercially available plasmid (pTM1) with Trp promoter for expressing in *Escherichia coli* was treated with restriction enzymes of HindIll and EcoRI to cut the plasmid. To the resulting cleavage sites, the synthesized DNA fragment obtained in Item (1) was ligered with use of DNA ligase to reconstruct a recombinant plasmid. This recombinant plasmid was named as "pTMH1". The plasmid has been designed to commence a protein synthesis at the expression plasmid with two motilin-like genes which are mutually connected through a peptide of Gly-Ile-Phe-Met. The resulting recombinant plasmid was named as "pTMH2".

In the above case, the cleavage sites by the restriction enzymes of BamH1 and BglIl were ligated with the DNA ligase, but each of the restriction enzymes can now not recognize the resulting ligated part, and thus a recombinant plasmid, wherein the motilin-like genes are tandemly arranged freely in number, has the leader peptide sequence through methionine in upper-stream of the motilin-like gene part, by repeating the operations as referred to above.

(4) Production of fused protein containing motilin-like polypeptide:

A recombinant plasmid with four tandemly arranged motilin-like genes (pTMH4, prepared by the manner as described in said Item 3) was inserted in *Escherichia coil* (HB101 strain) to cause a transformation thereof (The transformant was named as "*E. coli* MH4" and has been internationally deposited with Fermentation Research Institute, Agency of Industrial Science and Technology of Japan under the deposition number of -FERM BP-2555--). The transformants were cultivated at 30° C. in a medium containing 50 µg/ml of ampicillin (for instance, the medium prepared by adding 0.5% casamino acid in M9-medium), under aeration. At the time when $A_{550}$ became 0.6–0.8, indole acrylic acid (IAA) was added, final concentration thereof being made to 15 µg/ml.

Then the cultivation was continued for 16 hours and the resulting medium centrifuged (8000 rpm, 4° C., 5 minutes) to recover cells. A part of the cells was taken and analyzed by 15% polyamide-gel electrophores is to find out that desired fused protein reached about 30% of total protein. This brings such estimations of that the leader peptide sequence part of the synthetic DNA inserted in the plasmid accelerates efficient formation of the granulocytes and almost no decomposition by protease shall occur.

(5) Isolation and purification of motitin-like polypeptide:

A suspension of the paste-like cells obtained in said Item 4 (about 30 ml) and in 200 ml of cold acetone was filtered with use of a glass filter, and the resulting residue was suspended in 300 ml of saline and and then subjected to a high pressure homogenizer or ultra-sonic treatment to breakdown the cells. The resulting cell residue was centrifuged at 10000 rpm for 15 minutes to obtain a pellet. The pellet contains the fused protein consisting of the leader sequence pep tide and a tetramer of motilin-like polypeptide.

To a solution of the pellet (amount of protein; about 500 mg) in 30 ml of 70% formic acid, cyanogen bromide (500 mg) was added and reacted at 30° C. for overnight. To the reaction mixture, NaOH (40 g) and distilled water (200 ml) were added to set pH of the solution to a level not lower than 3. The solution was centrifuged (1000 rpm for 20 minutes) to recover aqueous phase. The solution was desalted with Sephadex G-15 column to remove the formic acid and cyanogen bromide, and motilin-like polypeptide fractions were treated by cation exchange chromatography and then purified by HPLC under following conditions and with use of µ Bondasphere C-18 column (19 mm×15 cm).

Eluate: Linear gradient of 30% to 60% acetonitrile in 0.1% trifluoroacetate, 30 minutes;

Flow rate: 7.0 ml/min.

Fractions in a main peak part on the HPLC were collected and lyophilized. A part of the dried powder was taken and checked with use of a peptide sequencer marketed by Applied Biosystems Co. to confirm that the sample has the desired motilin-like polypeptide having Hse at C-terminal and having the correct amino acid sequence.

By carrying out operations as above, 400mg–500 mg of the desired motilin-like polypeptide were obtained from one liter of the medium, in which the recombinant Escherichia coil (said *E. coli* MH4) was cultivated.

Biological Activity Test Example 1

An intestinal contraction activity was measured by Magnus method using upper small intestine of rabbit ["J. Pharm. Pharmac.", Vol. 28, pages 650–651 (1976)], on each motilin-like polypeptides (Example 1, wherein $R_1$ is Hse, Asp-Gly-Ile-Phe-Hse, or Arg-Ile-Phe-Hse) according to the invention, as test samples and a conventional pure [Leu$^{13}$]-motilin, as control sample. The activities of the test samples and control sample were compared, under assumption of that an contraction activity caused by $10^{-6}$ M acetylcholine is 100%.

Results are shown in FIG. 3. As apparently seen from the Figure, it has been confirmed that each of the polypeptides according to the invention has the intestinal contraction activity at the level same with or higher than that of the [Leu$^{13}$]-motilin.

Biological Activity Test Example 2

An intestinal contraction activity of various motilin analogues prepared in the manner similar to Example 1 was measured by Magnus method as in Biological Test Example 1 to determine $ED_{50}$ thereof and compared with that of native motilin, under assumption of that the contraction activity of the native motilin is 100%.

Results are shown in following Table 1. Please note that all of the motilin analogues given in the Table are designated as "Hse" at C-terminal, but the motilin analogues, wherein Hse is homoserine, homoserine-lactone or sodium salt thereof, showed substantially the same contraction activity level.

Further, motilin analogues, wherein Hse residue was changed to a radical of -OH, also showed the contraction activity at same level with those having Hse residue at C-terminal.

TABLE 1

| Activity in vitro (%) | | | | | |
|---|---|---|---|---|---|
| 1 | 5 | 10 | 15 | 20 | |
| Phe-Val-Pro-Ile-Phe-Thr-Tyr-Gly-Glu-Leu-Gln-Arg-Met-Gln-Glu-Lys-Glu-Arg-Asn-Lys-Gly-Gln | | | | | 100 |
| | | | (13) -Leu- | (23) -Hse | 100 |
| (3) -Gly- | | | -Leu- | -Hse | 170 |
| -Ser- | | | -Leu- | -Hse | 90–100 |
| -Asn- | | | -Leu- | -Hse | 90–100 |
| -Ile- | | | -Leu- | -Hse | 2 |
| | (8) -Ser- | | -Leu- | -Hse | 90–100 |
| | -Asn- | | -Leu- | -Hse | 90–100 |
| | -Ile- | | -Leu- | -Hse | 2 |
| | | (11) -Glu- | -Leu- | -Hse | 110 |
| | | -Asp- | -Leu- | -Hse | 100 |
| (2) -Leu- | | | -Leu- | -Hse | 100 |
| -Ile- | | | -Leu- | -Hse | 100 |

TABLE 1-continued

| | | | | Activity in vitro (%) | | | | |
|---|---|---|---|---|---|---|---|---|
| 1 | | 5 | 10 | | 15 | 20 | | |
| | | (4) -Leu- | | | -Leu- | | -Hse | 120 |
| | | -Val- | | | -Leu- | | -Hse | 100 |
| | | | (10) -Ile- | | -Leu- | | -Hse | 110 |
| | | | -Val- | | -Leu- | | -Hse | 100 |
| (1) Tyr- | | | | | | | | 100 |
| Ile- | | | | | | | | 10 |
| | | (5) -Tyr- | | | -Leu- | | -Hse | 100 |
| | | -Ile- | | | -Leu- | | -Hse | 10 |
| | | | | (7) -Phe- | -Leu- | | -Hse | 100 |
| | | | | -Ile- | -Leu- | | -Hse | 10 |
| | | | | | -Leu- | (19) -Glu- | -Hse | 90–100 |
| | | | | | -Leu- | -Asp- | -Hse | 90–100 |
| | | | | | -Leu- | | (22) -Arg-Hse | 90–100 |
| | | | | | -Leu- | | -Lys-Hse | 90–100 |

It can be found from the results shown in Table 1 that an activity can be increased by exchanging one or more amino acid residues, although it has been said that the pharmacological active part of the human motilin depends on amino acid sequence near N-terminal, the following may be said on the relation between the amino acid sequence near N-terminal and a degree of the activity.

a) The motilin analogues, wherein Pro in 3-position and Gly in 8-position of the native motilin are exchanged to Gly, Ser or Asn residue which can take a turn structure in the polypeptide chain, show the activity in the level same with or higher than that of the native motilin, but the activity remarkably reduces, when the amino acid residues in said positions were exchanged to Ile which is difficult to take the meander structure.

In the above case, the motilin analogues, wherein Pro in 3-position of the native motilin was exchanged to Gly, show quite high activity, namely about twice of the native motilin.

b) Although Val in 2-position, Ile in 4-position and Leu in 10-position of the native motilin are amino acids having a hydrophobic side-chain, motilin analogues having a structure of that these amino acids were mutually exchanged show the activity in the level same with or higher than that of the native motilin.

c) Although Phe in 1,5-position and Tyr in 7-position of the native motilin are amino acids having a side-chain with an aromatic ring, motilin analogues having a structure of that these amino acids were mutually exchanged show the activity in the same level with that of the native motilin, but if the amino acid in said positions was exchanged to another amino acid, for instance to Ile, remarkable reduction will occur in activity.

d) it has been considered that C-terminal part of the native motilin is constituted with amino acid residues with charge or polarity and is important for retaining the activity, particularly in vivo, although it is not main active part. Therefore, motilin analogues having an amine acid structure for increasing positive or negative charge at C-terminal and checked a biological activity thereof, but almost no change in activity was found. This brings an estimation of that the amine acid exchange in some extent, at the part near C-terminal does not give so high influence on the activity, if a charge-balance therein is kept throughout.

Biological Activity Test Example 3

Intestinal contraction activity (upper small intestine, jejunum and ileum) was measured by Balloon method using an unconscious dog, on the test sample of [Leu$^{13}$]-motilin-homoserine (Example 1, $R_1$: Hse) and the control sample of [Leu$^{13}$]-motilin which was chemically synthesized, when the sample was administered in an amount of 2.0 µg/kg/hr.

Figure 4A:
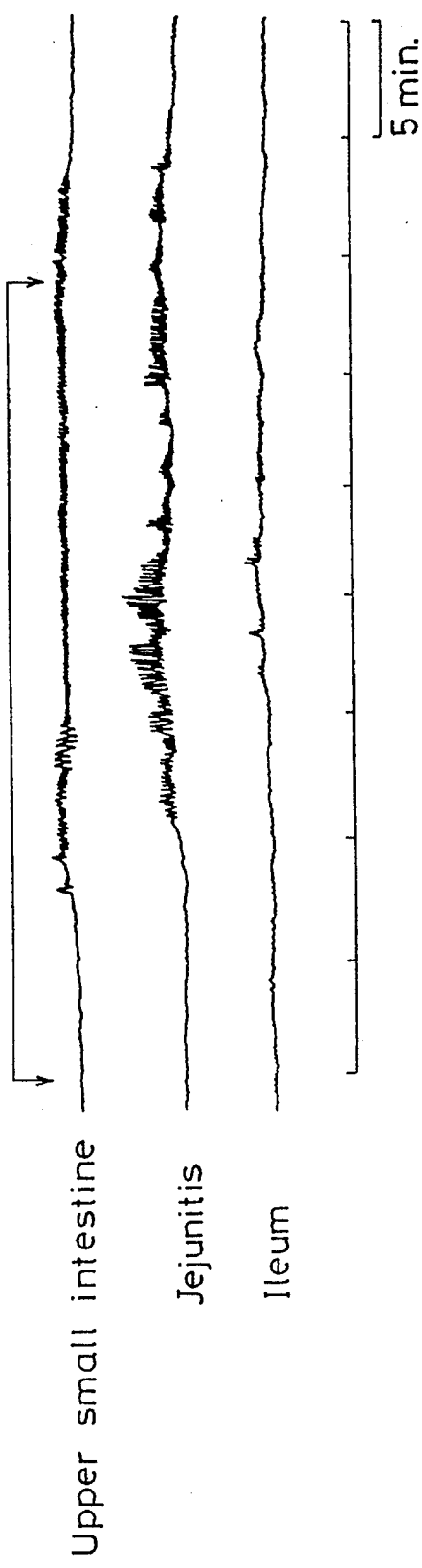
FIG. 4A is a chart showing a motional change of intestinal measured by Balloon method using an unconscious living dog, when [Leu$^{13}$]-motilin-homoserine according to the invention was administered.
Figure 4B:
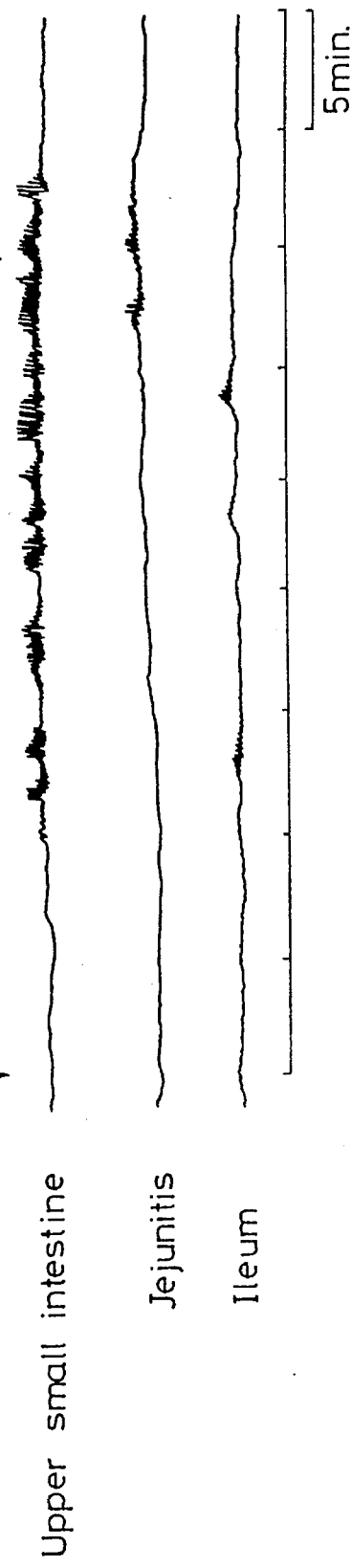
FIG. 4B is a chart similar to that of FIG. 4A, but shows the case of that the conventional pure [Leu$^{13}$]-motilin, as control, was administered.

Results are shown in FIGS. 4A and 4B. As apparently seen from the Figures, it was confirmed that the polypeptide according to the invention ([Leu$^{13}$]-motilin-homoserine) has a noticeable higher contraction activity than the control of [Leu$^{13}$]-motilin, and that the contraction activity of the polypeptide according to the invention appears in a natural manner.

Further, the polypeptides according to the invention and having homoserine-lactone residue in 23-position has the biological activity same with or similar to those having homoserine residue in 23-position.

Moreover, the polypeptides according to the invention and having various amine acid residues not exceeding 10 and containing Hse residue at C-terminal show the biological activity same with or similar to those having homoserine residue in 23-position.

Biological Activity Test Example 4

Contraction activity of upper small intestine was measured by Balloon method using an unconscious dog as in Biological Test Example 3, on the test sample of [Leu$^{13}$]-motilin-homoserine (Example 1, $R_1$: Hse, Test Sample 1) and its sodium salt (Test Sample 2) as well as the control sample of [Leu$^{13}$]-motilin, when the sample was administered in an amount of 2.0 µg/kg/hr, to calculate $ED_{50}$, and then compared under assumption of that the activity of the control sample is 100%.

Results are shown in following Table 2. As apparently seen from the Table, the test samples show the activity higher than the control sample, by 10%–20%.

TABLE 2

| Sample | Activity (%) |
|---|---|
| Control Sample | 100 |
| Test Sample | |
| 1 | 110–120 |
| 2 | 110–120 |

Biological Activity Test Example 5

Contraction activity of upper small intestine was measured by Balloon method using an unconscious dog as in Biological Test Example 3, on the test sample of [Leu$^{13}$]-motilin-homoserine (Example 1, $R_1$: Hse) and its sodium salt as well as the control samples of the conventional [Leu$^{13}$]-motilin and prostagrandin $F_{2\alpha}$ which has been clinically employed for curing gastroenteropathies, for instance "ileus", to calculate $ED_{50}$, and then compared under assumption of that the activity of the prostagrandin is 100%.

Figure 5:
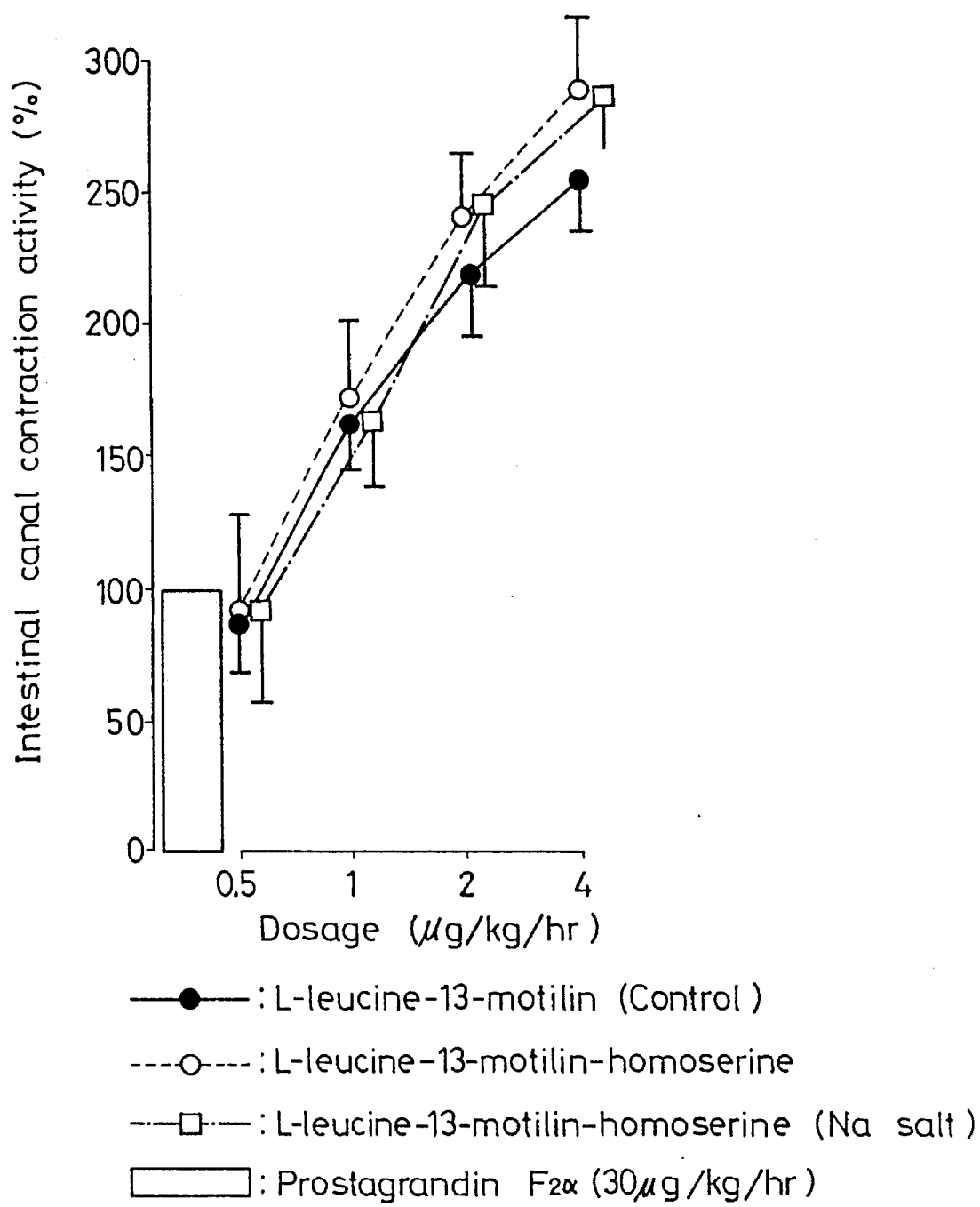
FIG. 5 is a graph showing results of that an intestinal canal contraction activity was measured by Balloon method and compared, on the conventional [Leu$^{13}$]-motilin, as control sample and [Leu$^{13}$]-motilin-homoserine and a salt thereof, as test samples, in various concentration, when a contraction activity of the conventional drug of 30 μg/kg/hr prostagrandin F$_{2\alpha}$ is assumed as 100%.

Results are shown in FIG. 5. As apparently seen from the Figure, the polypeptide and its salt according to the invention show the activity in far low concentration, when compared with the now widely accepted drug of prostagrandin, so that an amount for administration can be remarkably reduced, when the same effect shall be expected.

From FIGS. 4A and 4B, the polypeptides according to the invention and more particularly, [Leu$^{13}$-motilin-homoserine show the natural contracting action on intestin into consideration, it can be said that the invention provides a drug far excellent than the conventional drug of prostagrandin, in its safety and mild action.

Medicine Preparation Example

A solution of polypeptide according to the invention ([Leu$^{13}$]-motilin-homoserine, Example 1: Hse) in refined water was aseptically charged into vials, so that each vial contains the polypeptide by 1 mg. After lyophilized, the vial was sealed to obtain a dry powdery medicine. The powdery medicine is dissolved in saline or the like for injection purpose, when it shall be used.

What is claimed is:

1. A recombinant DNA for preparing a motilin analogue, comprising:

a single-stranded DNA encoding a leader sequence of the formula

Met-Thr-Met-Ile-Thr-Asn-Ser-Gln-Gln-Gln-Gln-Gln-Ile-Phe-Met and a subsequent sequence, encoding said motilin analogue, of the formula Phe—Val—A'—Ile—Phe—Thr—Tyr—B'—Glu—Leu—C— (III)
   —Arg—X'—Gln—Glu—Lys—Glu—Arg—D—Lys—Gly—E—Y"

wherein A' is Pro, Gly, Asn or Ser; B' is Gly, Pro, Asn or Ser; C is Gln, Glu or Asp; D is Asn, Glu or Asp, X' is a residue of amino acid other than Met; E is Gln, Lys or Arg; and Y" is a residue of Met or Met-Gly-Ile-Phe-Met,
   and its complementary single-stranded DNA.

2. An expression plasmid for preparing a motilin analogue, wherein said plasmid has an insert of synthetic double-stranded recombinant DNA, comprising:

a single-stranded DNA encoding a leader sequence of the formula

Met—Thr—Met—Ile—Thr—Asn—Ser—Gln—Gln—Gln—Gln—

Gln—Gln—Ile—Phe—Met and a subsequent sequence, encoding said motilin analogue, of the formula Phe—Val—A'—Ile—Phe—Thr—Tyr—B'—Glu—Leu—C— (III)
   —Arg—X'—Gln—Glu—Lys—Glu—Arg—D—Lys—Gly—E—Y"

wherein A' is Pro, Gly, Asn or Ser: B' is Gly, Pro, Asn or Ser; C is Gln, Glu or Asp, D is Asn, Glu or Asp, X' is a residue of amino acid other than Met; E is Gln, Lys or Arg; and Y" is a residue of Met or Met-Gly-Ile-Phe-Met
   and its complementary single-stranded DNA.

3. An expression plasmid for preparing a motilin analogue of the formula

Phe—Val—A'—Ile—Phe—Thr—Tyr—B'—Glu—Leu—C—Arg— (II)

X'—Gln—Glu—Lys—Glu—Arg—D—Lys—Gly—E—Y' wherein A' is Pro, Gly, Asn or Ser; B' is Gly, Asn or Ser; C is Gln, Glu or Asp; D is Asn, Glu or Asp, X' is a residue of amino acid other than Met; E is Gln, Lys or Arg; and Y' is a residue of homoserine or homoserine-lactone,
   wherein said plasmid has an insert of a synthetic double-stranded DNA comprising:

a single-stranded DNA encoding a leader sequence of the formula

Met—Thr—Met—Ile—Thr—Asn—Ser—Gln—Gln—Gln—Gln—

Gln—Gln—Ile—Phe—Met and a subsequent sequence, encoding said motilin analogue, of the formula Phe—Val—A'—Ile—Phe—Thr—Tyr—B'—Glu—Leu—C—Arg— (IV)

X'—Gln—Glu—Lys—Glu—Arg—D—Lys—Gly—E—Met—

Gly—Ile—Phe—Met—Phe—Val—A'—Ile—Phe—Thr—Tyr—

B'—Glu—Leu—C—Arg—X'—Gln—Glu—Lys—Glu—Arg—

D—Lys—Gly—E—Met—Gly—Ile—Phe—Met—Phe—Val—

A'—Ile—Phe—Thr—Tyr—B'—Glu—Leu—C—Arg—X'—

Gln—Glu—Lys—Glu—Arg—D—Lys—Gly—E—Met—Gly—

Ile—Phe—Met—Phe—Val—A'—Ile—Phe—Thr—Tyr—B'—

Glu—Leu—C—Arg—X'—Gln—Glu—Lys—Glu—Arg—D—

Lys—Gly—E—Y"

wherein A', B', D, X' and E are as previously defined, and Y" is a residue of Met or Met-Gly-Ile-Phe-Met as well as its complementary single-stranded DNA.

4. A process for the preparation of a motilin analogue of the formula:

Phe—Val—A'—Ile—Phe—Thr—Tyr—B'—Glu—Leu—C—Arg— (II)

X'—Gln—Glu—Lys—Glu—Arg—D—Lys—Gly—E—Y' wherein A' is Pro, Gly, Asn or Ser; B' is Gly, Asn or Ser; C is Gln, Glu or Asp; D is Asn, Glu or Asp, X' is a residue of amino acid other than Met; E is Gln, Lys or Arg; and Y' is a residue of homoserine or homoserine-lactone, or a salt thereof, comprising the following steps:

(a) synthesizing a single-stranded DNA fragment coding for a leader polypeptide of the formula Met—Thr—Met—Ile—Thr—Asn—Ser—Gln—Gln—Gln—Gln—
                                                                Gln—Gln—Ile—Phe—Met and its complementary single-stranded DNA fragment;

(b) annealing said single-stranded DNA fragment to its complementary single-stranded DNA fragment to form a double-stranded DNA fragment;

(c) synthesizing a single-stranded DNA fragment, encoding a motilin analogue having the formula Phe—Val—A'—Ile—Phe—Thr—Tyr—B'—Glu—Leu—C—   (III)
—Arg—X'—Gln—Glu—Lys—Glu—Arg—D—Lys—Gly—E—Y"

wherein A', B', C, X' and E are as previously defined;
and Y" is a residue of Met or Met-Gly-Ile-Phe-Met
and its complementary single-stranded DNA fragment;

(d) annealing said single-stranded DNA fragment to its complementary single-stranded DNA fragment to form a double-stranded DNA fragment;

(e) ligating the double-stranded DNA fragments;

(f) adding a specific restriction site to each terminal end of the resulting double-stranded DNA fragment;

(g) cleaving a plasmid with restriction enzymes;

(h) ligating said double-stranded DNA fragment to each cleavage site of the cleaved plasmid to construct a recombinant plasmid;

(i) cutting said recombinant plasmid upstream of the synthetic double-stranded DNA insert by treating said plasmid with two restriction enzymes to recover a fragment comprising said synthetic DNA;

(j) cutting a second recombinant plasmid as above, with said restriction enzymes;

(k) ligating said fragment, in tandem arrangement, to the cleavage sites in said second plasmid using DNA ligase;

(l) repeating the above steps to construct a plasmid encoding four genes;

(m) inserting the plasmid into a prokaryote to cause a transformation thereof;

(n) cultivating the resulting transformant to produce therein a polypeptide encoded by said double-stranded DNA fragment of step (b) and a polypeptide encoded by said double-stranded DNA fragment of step (d);

(o) lysing the transformant and treating the same with cyanogen bromide to separate the polypeptides of the fused protein;

(p) fractionating the resulting mixture to isolate the desired polypeptide; and (q) optionally converting the polypeptide into a salt.

* * * * *

UNITED STATES PATENT AND TRADEMARK OFFICE
CERTIFICATE OF CORRECTION

PATENT NO.  : 5,459,049
DATED       : October 17, 1995
INVENTOR(S) : Kurono et al.

It is certified that error appears in the above-identified patent and that said Letters Patent is hereby corrected as shown below:

Title page, [75] line 1 change "Matani" to read -- Mitani --.

[30] after line 2, insert line 3 as -- Aug. 24, 1989 [JP]  Japan .............1-216033

Signed and Sealed this

Thirtieth Day of January, 1996

Attest:

BRUCE LEHMAN

Attesting Officer

Commissioner of Patents and Trademarks